United States Patent [19]
Bacon, Jr. et al.

[11] Patent Number: 5,095,206
[45] Date of Patent: Mar. 10, 1992

[54] METHOD AND APPARATUS FOR IMPROVING THE SPECIFICITY OF AN ION MOBILITY SPECTROMETER UTILLIZING SULFUR DIOXIDE DOPANT CHEMISTRY

[75] Inventors: Allan T. Bacon, Jr., Joppatowne; Julio A. Reategui, Hunt Valley, both of Md.

[73] Assignee: Environmental Technologies Group, Inc., Baltimore, Md.

[21] Appl. No.: 687,594

[22] Filed: Apr. 17, 1991

Related U.S. Application Data

[63] Continuation-in-part of Ser. No. 534,701, Jun. 1, 1990, Pat. No. 5,032,721.

[51] Int. Cl.$^5$ .................... B01D 59/44; H01J 49/40
[52] U.S. Cl. .................... 250/282; 250/286; 250/287; 250/288
[58] Field of Search .................... 250/281, 282, 286, 287, 250/288

[56] References Cited

U.S. PATENT DOCUMENTS

| | | | |
|---|---|---|---|
| 3,717,028 | 2/1973 | Annino et al. | 73/23.36 |
| 4,390,784 | 6/1983 | Browning et al. | 250/286 |
| 4,445,038 | 4/1984 | Spangler et al. | 250/287 |
| 4,797,554 | 1/1989 | Blanchard et al. | 250/287 |
| 4,839,143 | 6/1989 | Vora et al. | 250/281 |

Primary Examiner—Bruce C. Anderson
Attorney, Agent, or Firm—Leonard Bloom

[57] ABSTRACT

An improved ion mobility spectrometer (IMS) and method for operating the same which enables analysis of a specific acid gas analyte in a mixture of such gases when air is used as the carrier gas and the drift gas in the IMS. A controlled concentration of sulfur dioxide dopant is added to the air carrier gas stream prior to application of the carrier gas stream. In the IMS, the drift times of the ions generated from the doped air carrier gas differ from the drift times of the ions generated from the acid gas analyte, thereby enabling identification and quantification of the analyte.

34 Claims, 3 Drawing Sheets

METHOD AND APPARATUS FOR IMPROVING THE SPECIFICITY OF AN ION MOBILITY SPECTROMETER UTILLIZING SULFUR DIOXIDE DOPANT CHEMISTRY

CROSS-REFERENCE TO RELATED APPLICATIONS

This application is a continuation-in-part of application Ser. No. 534,701, filed June 1, 1990 U.S. Pat. No. 5,032,721.

FIELD OF THE INVENTION

The present invention relates to the use of ion mobility spectrometry for detecting certain acid gasses in air, and more particularly, to the use of sulfur dioxide dopant for improving the specificity of detection of certain acid gasses such as chlorine, hydrogen chloride and other gasses which have high charge affinities.

BACKGROUND OF THE INVENTION

There is a pressing need in industry for a monitoring system capable of identifying and quantifying trace quantities of hazardous gasses escaping into the air. The monitors, located in the vicinity of processing plants and storage facilities, provide early warning of impending danger to plant personnel and to the public, and they enable corrective action to be taken in time to avoid disaster. An ideal monitoring system is capable of operating unattended continuously for extended periods of time without the need for frequent maintenance or calibration. Monitoring systems in present use electrochemical cells and other devices as the sensing element. Such systems are inadequate in some applications because they lack specificity, require frequent maintenance for calibration and replenishment of electrolyte, and many are limited to operation at ambient temperatures above 0° C. (due to freezing of the electrolyte).

The Ion Mobility Spectrometer (IMS) is an accepted analytical tool capable of identifying and quantifying trace amounts of a substance in a sample. Basically, an IMS comprises an analyzer cell, means for ionizing samples of an analyte admitted to the cell and means for determining the times required for the ions of the various substances present in the cell to traverse a specific length of the cell under the influence of an electric field and against the force of a stream of drift gas flowing through the cell in a direction opposite to that of the electric field. A representative analyzer cell is disclosed in U.S. Pat. No. 4,390,784 issued to Browning et al. A stream of purified air or other gas may be used as a carrier gas to introduce the analyte sample into the cell, and a stream of purified air or other gas may also be used as the drift gas. Both the carrier gas and the drift gas are therefore readily available at an installation site in unlimited quantities and no maintenance is required of the sensor other than the occasional replacement of filters and membranes for purifying the carrier and drift gasses, radiation wipe tests and calibration. An IMS therefore appears to be the ideal sensor for use in a monitoring system.

However, it has been found that an IMS operated in a conventional manner, using air as the carrier and drift gasses, may lack the specificity necessary to detect many of the acid gasses of interest, such as hydrogen fluoride, hydrogen chloride, nitrogen dioxide, and others. The reason for such lack of specificity is that the ion peak characteristic of pure air alone and the ion peak characteristic of the analyte gas in air both arrive at the ion detector of the IMS at virtually the same times. The pure air ion peak disrupts the analyte peak, especially when the analyte is an acid gas. Hence, it becomes very difficult to distinguish the amplitude of the ion current due to the acid gas from the ion current due to pure air at a given arrival time.

In application Ser. No. 534,701 now U.S. Pat. No. 5,032,221, a monitor having improved specificity for acid gasses was described. The disclosed acid gas monitor makes use of a dopant selected from the group of substituted phenols. The dopant improves the ability of the gas monitor to detect the general presence of acid gasses such as hydrogen flouride, hydrogen chloride, chlorine, nitrogen dioxide, sulfur dioxide, carbonyl sulfide, and numerous others. This ability to detect the presence of acid gas proves advantageous in many situations. However, it is often desireable to identify the presence of a specific type of acid gas, and to quantify the amount of the specific acid gas. The acid gas monitor in application Ser. No. 534,701 now U.S. Pat. No. 5,032,721 provides the requisite specificity to detect certain types of acid gas (such as HF), but it lacks the specificity for others. If more than one acid gas is present, the specificity is inadequate to distinguish between the gases. For example, if chlorine is being monitored and another acid gas is present, the device may give a false indication of the presence of chlorine or its concentration.

SUMMARY OF THE INVENTION

It is, therefore, an object of the present invention to provide a method of ion mobility spectrometry with improved specificity for detecting certain gasses, whereby interference and false indications resulting from coexisting gasses is eliminated.

It is another object of the present invention to provide a method and apparatus based on ion mobility spectrometry which detects chlorine, hydrogen chloride and other gasses having a high charge affinity with a very high degree of specificity.

It is a further object of the invention to provide a system for monitoring acid gasses which is not responsive to other gasses such as sulfur dioxide, carbonyl sulfide and like gasses having a low charge affinity.

It is still another object of the invention to provide an acid gas monitor capable of indicating the presence and quantity of specific types of hazardous gasses in a mixture of gasses.

According to the present invention, the above-described and other objects are accomplished by providing an ion mobility spectrometer with improved specificity for detecting certain gases, and a method for operating the same. The spectrometer includes an analyzer cell having an inlet region, a reaction region, an ionization source in said reaction region, a shutter grid, a drift region, an ion current detector for detecting ions transiting said cell drift region, and means for measuring the transit times through the cell drift region of ions generated in the cell reaction region and released into the drift region through the shutter grid. The method of operation includes the steps of applying a drift gas stream of air to the cell drift region, mixing sulfur dioxide with a carrier gas stream of air to create a doped carrier gas stream, introducing a test sample of gas into the analyzer cell inlet region, applying the carrier gas stream to the cell inlet region to carry the test sample into the cell reaction region, measuring an ion current at the ion current detector at a time corresponding to the transit time through the cell drift region of ions generated by the test sample in the cell reaction region. The sulfur dioxide dopant used in this method causes ions generated by said carrier gas stream in the cell reaction region to have transit times through said cell drift region which are different from the transit times through the cell drift region of ions generated by the test sample. At the same time, the sulfur dioxide dopant suppresses ion current attributable to acid gasses with low charge affinities, thereby improving the specificity for acid gasses having high charge affinities.

The specificity is improved for certain acid gases such as $Cl_2$ and $HCl_2$, but detection is not achieved for other gases such as HF, COS, and $SO_2$. For these, the substituted phenol dopant chemistry of application Ser. No. 534,701 provides detection capability. Hence, the present invention would be advantageous in certain situations, and the invention of application Ser. No. 534,701 is advantageous in others.

BRIEF DESCRIPTION OF THE DRAWINGS

Other objects, features and advantages of the present invention will become more apparent from the following detailed description of preferred embodiments and certain modifications thereof when taken together with the accompanying drawings, in which.

DETAILED DESCRIPTION OF THE INVENTION

Figure 1:
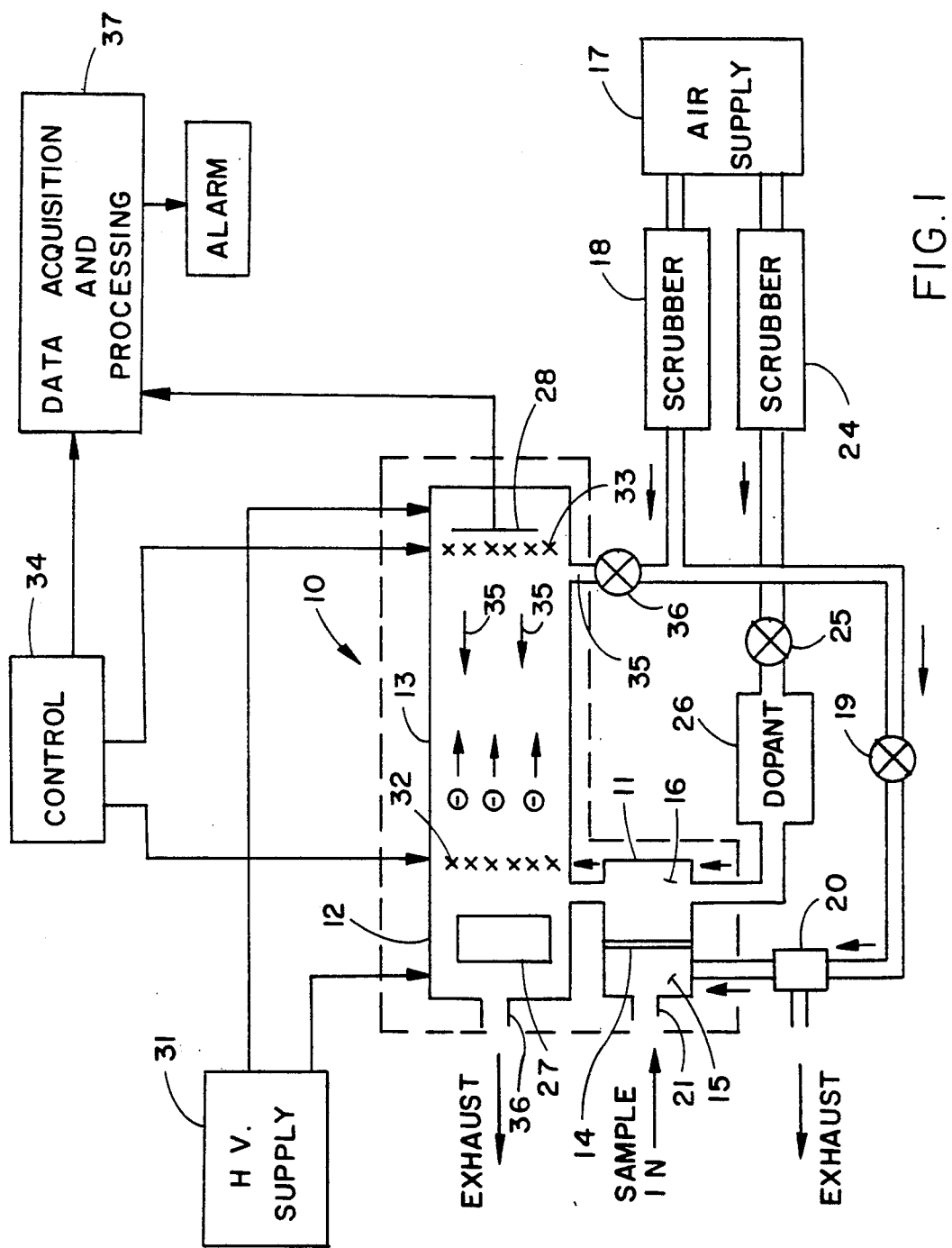
FIG. 1 is a functional block diagram, partially in schematic form, of an Ion Mobility Spectrometer used in the practice of the method of the invention.

Referring to FIG. 1, the apparatus used in the practice of the method of the invention comprises a conventional IMS analyzer cell 10 such as disclosed in U.S. Pat. No. 4,390,784 issued to Browning et al. Cell 10 is divided into an inlet region 11, a reaction region 12 and a drift region 13. Inlet region 11 is partitioned by a permeable membrane 14 into a sample chamber 15 and an inlet chamber 16. Air from a regulated pressure air supply 17 is passed through a scrubber 18, flow regulator 19 and venturi 20 and through sample chamber 15 to an exhaust 21. The air flow through venturi 20 and sample chamber 14 inducts a sample gas into sample chamber 14. Membrane 14 allows passage of the constituents of interest into inlet chamber 15 while excluding interferant substances from chamber 15. Those constituent substances passing through membrane 14 into chamber 15 are swept from chamber 15 by a carrier gas into the reaction region 12 of analyzer cell 10.

In accordance with the invention, the carrier gas comprises air from air supply 17 that is passed through a scrubber 24 primarily to remove water vapor therefrom, and through flow regulator 25, and a permeation tube 26, where a controlled concentration of sulfur dioxide ($SO_2$) dopant is added to the air.

Reaction region 12 contains a source 27 of $\beta$-particle ionizing radiation which generates product ions from the constituents swept into region 12 by the carrier gas. Source 27 is usually formed of a ring of Ni63. The product ions formed in region 12 are driven in the direction of an ion detector 28, located at the end of drift region 13 opposite reaction region 12, by an electrostatic field applied along regions 12 and 13 by a high voltage supply 31. Reaction region 12 is partitioned from drift region 13 by a shutter grid 32, and ion detector 28 is separated from drift region 13 by an aperture grid 33. Shutter grid 32 and aperture grid 33 are separately biased by voltages from a control circuit 34. A drift gas, admitted to drift region 13 through port 35, flows continuously through drift region 13 and reaction region 12, exhausting therefrom through exhaust vent 36. The drift gas comprises air from air supply 17 passed through scrubber 18 and flow regulator 36 into port 35.

In the conventional mode of operating an IMS for the detection of negative ions, shutter grid 32 is biased negatively for the major part of a scan cycle to block the product ions in reaction region 12 from entering drift region 13. At the beginning of a scan period, the bias is changed briefly to allow a cloud of ions to enter drift region 13. The ions drift along the length of drift region 13 under the influence of the electric field and against the force of the counter-flowing drift gas, represented by the arrows 35 toward the detector 28.

The product ions created by the various constituents traverse the drift region in different time periods, depending upon the charge/molecular size characteristics of each constituent. If a complete spectrum is to be taken, aperture grid 33 may be neutrally biased so that the arrival times of each of the various ion groups at detector 33 may be measured. If the IMS is intended to be responsive to only a single specific substance, the aperture grid may be biased so as to repel all ions except for those arriving at a time corresponding to the predetermined characteristic arrival time of ions for the substance of interest.

Alternatively, the IMS may be operated in the enhancement mode, as disclosed and claimed in U.S. patent application Ser. No. 344,128; filed April 27, 1989 by J. A. Reategui et al. for "Method and Apparatus for Enhanced Ion Spectrum Generation and Detection in Ion Mobility Spectrometry", assigned to the assignee of the present application. Briefly, in the enhancement mode, the shutter grid 32 of the IMS is biased open for the major portion of a scan cycle allowing ions to enter drift region 13 continuously upon their generation in the cell reaction region 12. At the beginning of a scan cycle, the shutter grid 32 is momentarily biased closed, thereby creating a void in the otherwise continuous stream of ions transiting from reaction region 12 into drift region 13. The void traverses drift region 13 and becomes separated into secondary voids which arrive at ion detector 33 at different transit times, in much the same manner as the ion groups which traverse and become separated in the conventional mode. The substantially steady stream of ions that enters drift region 13 during the open period of the shutter grid establishes a baseline ion current at detector 33. The arrival of a secondary void at detector 33 creates a negative peak in the base line current. The arrival time at detector 33 of a negative peak characterizes the identity of one constituent substance of the test sample, and the amplitude of the negative peak characterizes the concentration of the constituent substance in the test sample. Operation of an IMS in the enhancement mode has the advantages of producing better resolution of the separated ion current peaks and of providing a means permitting continuous calibration of the IMS. Operation of the IMS in the enhancement mode is preferred in the practice of the present invention, although the invention is equally applicable to the operation of an IMS in the conventional mode.

Data acquisition and processing unit 37 collects and averages the peak ion current amplitudes occurring at the arrival times that are characteristic of the analyte for a number of successive scans in order to determine whether the analyte concentration has reached the alarm level. When the analyte is chlorine in air, the monitoring system described above requires about 10 minutes for the average peak ion current to stabilize at an equilibrium level.

A more rapid measurement can be obtained by processing the data using an algorithm which includes a derivative term in order to predict the equilibrium value of the average peak ion current. A look-up table is first prepared containing values of the ratio of the ion current peaks obtained at the arrival times of the analyte ions and of the doped carrier gas reactant ions for a number of successive scans using known concentrations of analyte.

When a sample having an unknown mixture and concentration of analytes is tested, the respective ion current peaks are collected at one second intervals, suitably, and are processed to show the change in ion current over time. For example, the following algorithm may be employed for this purpose:

$$T_t = \left(\frac{A_s}{A_r}\right)_t + \sum_{(n=1)}^{(n=60)} \left[\left(\frac{A_s}{A_r}\right)_t - \left(\frac{A_s}{A_r}\right)_{t-1}\right]_n$$

where:

$T_t$ is the table look-up value at time t;
$A_s$ is the peak ion current amplitude at the arrival time of a specific analyte ion; and
$A_r$ is ion current amplitude at the arrival time of the doped carrier gas ion.

The look-up table will yield the concentration of the specific analyte of interest when entered at the value obtained for $T_t$ using the above algorithm.

Obviously, variations in the method of the invention are possible in the light of the above teachings. It is therefore to be understood that the invention may be practiced otherwise than as specifically disclosed without departing from the spirit and scope of the appended claims.

Figure 2:
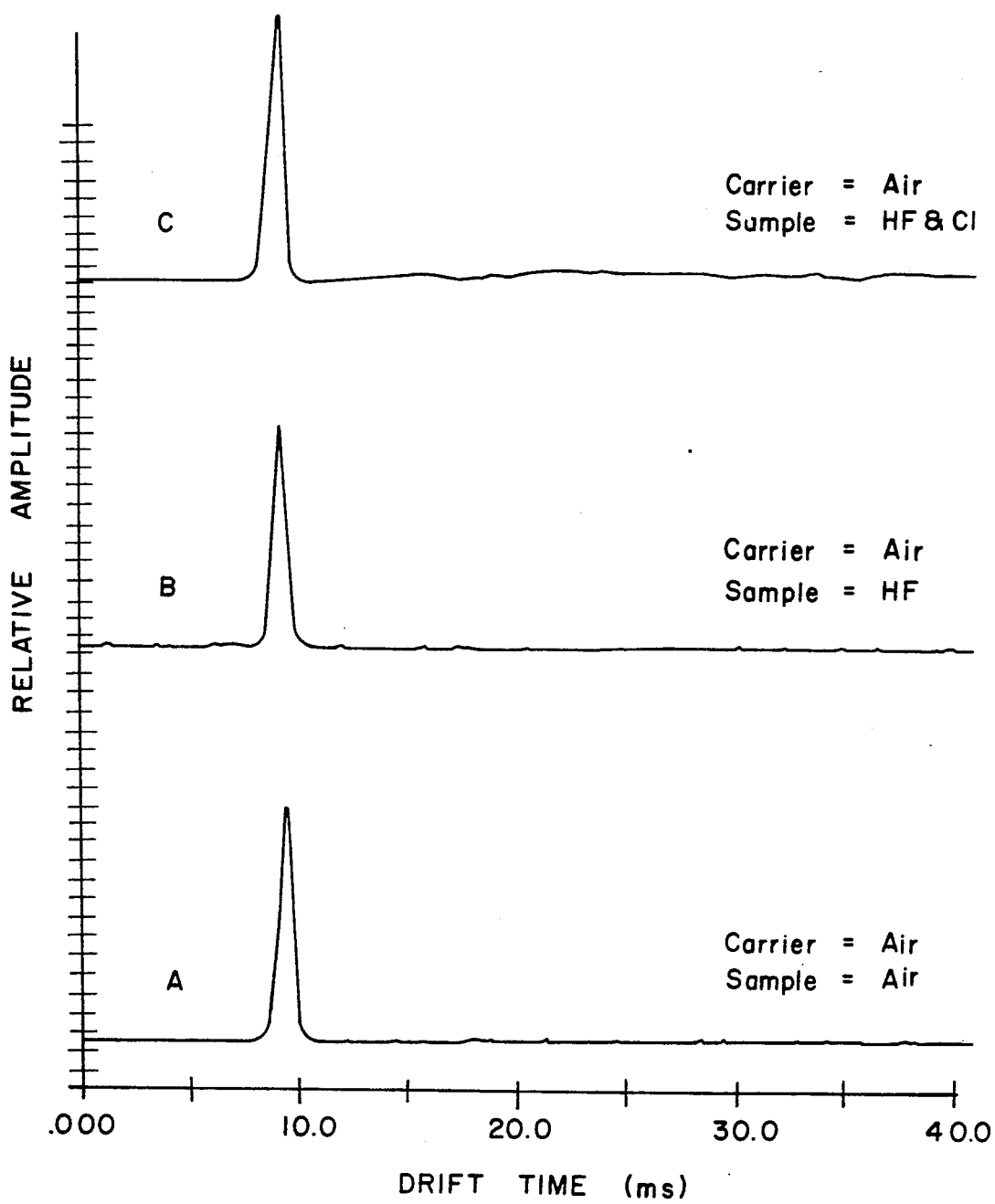
FIG. 2 is a comparative spectrograph showing of a conventional IMS showing the ion current peaks produced when purified air alone is used the carrier gas and varying types of acid gas analytes are present in the test sample.

FIG. 2 is a comparative spectrograph showing, in line A, the ion current peak produced when purified air alone is used the carrier gas in an IMS operated in the enhancement mode and no acid gas analyte is present in the test sample. The ion current peak appears at an arrival time of approximately 9.8 milliseconds (ms). Line B of FIG. 2 shows the ion current peak produced when purified air alone is used as the carrier gas in the IMS and an acid gas analyte, specifically hydrogen fluoride, is present in the test sample. The peak in line B occurs at substantially the same arrival time as that in line A, demonstrating the impracticality of using an IMS for the purpose of identifying an acid gas analyte when purified air alone is used as the carrier gas. As discussed, application Ser. No. 534,701, sets forth a partial solution to this problem in a monitor having improved specificity for acid gasses. The disclosed monitor makes use of a dopant selected from the group of substituted phenols. The dopant improves the ability of the gas monitor to detect the general presence of acid gasses such as hydrogen flouride. Hence, the hydrogen fluoride of line B can be distinguished from the purified air carrier gas. However, it is also desireable to identify the presence of a specific type of acid gas, and to quantify that type, in a test sample which includes a mixture of different acid gasses. The monitor shown in application Ser. No. 534,701 is incapable of this due to the interference caused by the other acid gases.

Line C of FIG. 2 shows the ion current peak produced when purified air alone is used as the carrier gas in the IMS and a mixture of acid gas analytes, specifically hydrogen fluoride and chlorine, are present in the test sample. The peak in line C occurs at substantially the same arrival time as that in lines A and B, demonstrating the impracticality of using an IMS for the purpose of identifying or quantifying the chlorine when another acid gas analyte (hydrogen flouride) is present. Similarly, when sulfur dioxide, carbonyl sulfide and other acid gasses are present, they will steal charge from the ion current peak produced by the chlorine, thereby decreasing specificity. The resulting specificity is decreased to the point where the method disclosed in application Ser. No. 534,701 cannot distinguish between these acid gasses. Instead, the method may give a false indication of the presence of chlorine or its concentration.

The present invention uses a sulfur dioxide dopant to eliminate or reduce the interference from ion peaks attributable to acid gasses having a low charge affinity (e.g. hydrogen fluoride, sulfur dioxide and carbonyl sulfide), thereby improving the IMS specificity for acid gasses having a high charge affinity (e.g. chlorine and hydrogen chloride).

Figure 3:
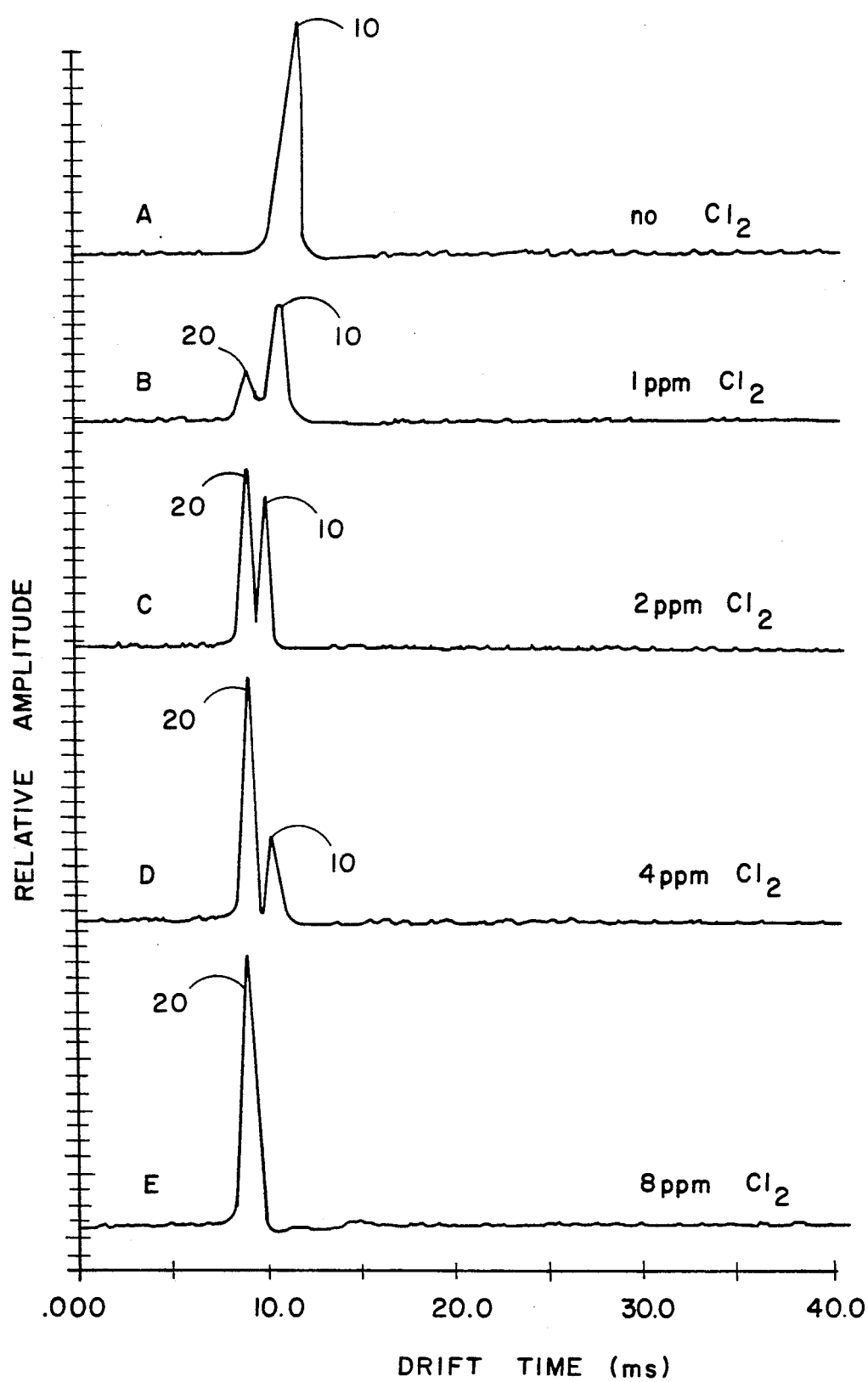
FIG. 3 is a comparative spectrograph produced by an IMS operated in the enhancement mode in accordance with the method of the present invention.

FIG. 3 is a comparative spectrograph produced by an IMS operated in the enhancement mode in accordance with the method of the present invention. A small concentration of sulfur dioxide dopant has been added to the purified air carrier gas prior to its admission to the IMS. In line A, the arrival time of the principal ion current peak 10 resulting from the air carrier gas with sulfur dioxide dopant added and no analyte is approximately 10.4 ms. Lines B-E of FIG. 3 show the results of introducing increasingly greater concentrations of analyte, specifically chlorine, using air with sulfur dioxide added as the carrier gas. The ion current peak 20 resulting from the presence of the analyte remains centered at approximately 9.5 ms for the increasing concentrations. Similarly, the ion current peak 10 resulting from the air carrier gas with sulfur dioxide added remains centered at approximately 10.4 ms. The decreasing amplitude of the 10.4 ms peak 10 which occurs as the amplitude of the 9.5 ms peak 20 increases is a manifestation of the principle of conservation of charge, as will be understood by those skilled in the art.

FIG. 3 demonstrates that an IMS operated in accordance with the method of the invention can serve effectively as the sensor in a monitoring system to detect trace amounts of chlorine in the atmosphere using air as the drift gas and air with sulfur dioxide dopant as the carrier gas. The method of the invention has also been shown to be effective for the detection of hydrogen chloride and other acid gasses.

The conditions under which the results of FIG. 3 were obtained were as follows:
carrier gas flow—140 cc/min; drift gas flow—250 cc/min; sulfur dioxide concentration—1 ppm (in carrier); drift region length—3.7 cm.; sampling rate—500 cc/min; reaction region electric field—125 V/cm.; drift region electric field—125 V/cm. inlet membrane—microporous teflon coated with one of OV210 or OV101, both available from Altech Associates, Deerfield, Ill. (as will be appreciated to one skilled in the art, different types of coatings are used to obtain different degrees of specificity and sensitivity, depending on the application); negative ion mode; enhanced shutter mode; shutter grid pulse width—200 us.

It should be limited that none of the above parameters are limiting, and that the invention can be practiced with wide deviations therefrom.

The method of the invention has also been shown to be equally effective for detecting chlorine, hydrogen chloride and other gasses (having a high charge affinity) with a very high degree of specificity from among a test sample which also contains sulfur dioxide, carbonyl sulfide or certain other gasses. Sulfur dioxide doping renders the ion mobility spectrometer non-responsive to gasses having low charge affinities. For example, the comparative spectrograph of FIG. 3 would appear the same even if HF, COS or $SO_2$ were present in the sample gas in addition to the $CL_2$. The HF, COS or $SO_2$ would not interfere with the ion current peaks 20 attributable to the $CL_2$.

We claim:

1. An improved method for operating an ion mobility spectrometer using air as a carrier gas and as a drift gas, said spectrometer comprising an analyzer cell having an inlet region, a reaction region, an ionization source in said reaction region, a shutter grid, a drift region, an ion current detector for detecting ions transiting said cell drift region, and means for measuring the transit times through said cell drift region of ions generated in said cell reaction region and released into said cell drift region through said shutter grid, the method comprising the steps of:
    applying a drift gas stream of air to said cell drift region;
    mixing sulfur dioxide with a carrier gas stream of air to create a doped carrier gas stream;
    introducing a test sample of gas into said analyzer cell inlet region;
    applying said carrier gas stream to said cell inlet region to carry said test sample into said cell reaction region; and
    measuring an ion current at said ion current detector at a time corresponding to the transit time through said cell drift region of ions generated by said test sample in said cell reaction region;
    whereby said sulfur dioxide dopant causes ions generated by said carrier gas stream in said cell reaction region to have transit times through said cell drift region which are different from the transit times through said cell drift region of ions generated by the test sample.

2. The improved method according to claim 1, whereby said step of mixing sulfur dioxide suppresses a componant of said measured ion current attributable to ions generated by test sample acid gasses with low charge affinities, said measured ion current being attributable mainly to ions generated by test sample acid gasses with high charge affinities.

3. The improved method of claim 1, wherein: said test sample comprises hydrogen fluoride.

4. The improved method as claimed in claim 1, wherein: said test sample comprises sulfur dioxide.

5. The improved method as claimed in claim 1, wherein: said test sample comprises carbonyl sulfide.

6. The improved method of claim 1, wherein: said step of mixing sulfur dioxide comprises mixing sulfur dioxide dopant in said carrier stream of air at a concentration of approximately 1 part per million.

7. The improved method of claim 1 wherein: said step of mixing sulfur dioxide with said carrier gas stream of air is accomplished by using a sulfur dioxide permeation tube immersed in said carrier gas stream, whereby said carrier gas mixes with sulfur dioxide permeating through said tube.

8. The improved method of claim 1, wherein said ion mobility spectrometer is operated in a negative ion mode.

9. An improved method for operating an ion mobility spectrometer using air as a carrier gas and as a drift gas, said spectrometer comprising an analyzer cell having an inlet region, a reaction region, an ionization source in said reaction region, a shutter grid, a drift region, an ion current detector for detecting ions transiting said cell drift region, and means for measuring the transit times through said cell drift region of ions generated in said cell reaction region and released into said cell drift region through said shutter grid, the method comprising:
    introducing a test sample of gas into said analyzer cell inlet region;
    applying a carrier gas stream to said cell inlet region to carry said test sample into said cell reaction region;
    applying a drift gas stream of air to said cell drift region;
    mixing sulfur dioxide with said drift gas stream of air to create a doped drift gas stream for carrying product ions generated by said test sample in said cell reaction region into said cell drift region; and
    measuring a product ion current at said ion current detector at a time corresponding to the transit time through said cell drift region of said product ions;
    whereby said sulfur dioxide dopant causes ions generated by said drift gas in said cell reaction region to have transit times through said cell drift region which are different from the transit times through said cell drift region of ions generated by the test sample.

10. The improved method according to claim 9, whereby said step of mixing sulfur dioxide suppresses a componant of said measured ion current attributable to ions generated by test sample acid gasses with low charge affinities, said measured ion current being attributable mainly to ions generated by test sample acid gasses with high charge affinities. ions generated by test sample acid gases with high charge affinities to have transit times through said cell drift region which are different from the transit times through said cell drift region of product ions generated by test sample acid gasses with low charge affinities.

11. The improved method as claimed in claim 9, wherein: said test sample comprises hydrogen fluoride.

12. The improved method as claimed in claim 9, wherein:
said test sample comprises sulfur dioxide.

13. The improved method as claimed in claim 9, wherein:
said test sample comprises carbonyl sulfide.

14. The improved method of claim 9, wherein:
said step of introducing sulfur dioxide comprises introducing sulfur dioxide in said drift gas stream of air at a concentration of approximately 1 part per million.

15. The improved method of claim 9, wherein:
said step of mixing sulfur dioxide with said drift gas stream of air is accomplished by using a sulfur dioxide permeation tube immersed in said drift gas stream, whereby said drift gas mixes with sulfur dioxide permeating through said tube.

16. The improved method of claim 9, further comprising the step of:
mixing sulfur dioxide with said carrier gas stream of air to create a doped carrier gas stream.

17. The improved method as claimed in claim 9, wherein said ion mobility spectrometer is operated in a negative ion mode.

18. An ion mobility spectrometer for analyzing an acid gas in a test sample, comprising:
an inlet region for inputting a test sample of gas;
a reaction region in fluid communication with said inlet region;
means for applying a carrier gas stream of air to said inlet region for carrying said test sample therefrom into said cell reaction region;
doping means for introducing sulfur dioxide into said carrier gas stream of air;
an ionization source in said reaction region for generating product ions from the test sample carried into the reaction region by said carrier gas;
a drift region through which said product ions travel in accordance with a charge and molecular size characteristic;
a shutter grid for selectively releasing said product ions from said reaction region into said drift region;
an ion current detector for detecting product ions transiting said cell drift region;
means for measuring a transit time through said cell drift region of product ions generated in said cell reaction region and released into said cell drift region through said shutter grid; and
means for measuring an ion current detected by said cell ion current detector at a time corresponding to the drift time of ions generated from said analyte gas in said cell reaction region;
whereby sulfur dioxide dopant introduced by said doping means causes ions generated by said carrier gas stream in said cell reaction region to have transit times through said cell drift region which are different from the transit times through said cell drift region of ions generated by the test sample.

19. The ion mobility spectrometer according to claim 18, whereby said sulfur dioxide dopant suppresses a componant of said measured ion current attributable to ions generated by test sample acid gasses with low charge affinities, said measured ion current being attributable mainly to ions generated by test sample acid gasses with high charge affinities.

20. The apparatus according to claim 18, wherein said sulfur dioxide doping means comprises a gas permeable tube immersed in said carrier gas stream for allowing dopant contained therein to permeate into said carrier gas stream.

21. The apparatus according to claim 20, wherein said gas permeable tube introduces said dopant to said carrier gas at a rate of about 365 nanograms per minute.

22. The apparatus according to claim 18, wherein said inlet region is partitioned by means for preventing passage of select constituents of said test sample.

23. The apparatus according to claim 22, wherein said partition means is a gas-permeable membrane.

24. The apparatus according to claim 18, further comprising processing means for computing a quantity of an acid gas constituent in said test sample based on said ion current measured by said ion current measurement means.

25. The apparatus according to claim 24, wherein said processing means further comprises a memory for storing expected peak ion current data characteristic of said constituent acid gas in said test sample, said processing means comparing actual measured ion currents detected by said cell ion current detector to said expected peak ion current data and quantifying said constituent based on said comparison.

26. The apparatus according to claim 25, wherein said expected peak ion current data comprises a calibration curve relating said actual measured ion currents to said constituent concentration.

27. An ion mobility spectrometer for analyzing an acid gas in a test sample, the spectrometer comprising:
an inlet region for introduction of said test sample of gas, said inlet region having means for allowing a limited amount of said test sample to penetrate;
a reaction region in fluid communication with said inlet region;
an ionization source in said reaction region for generating product ions from the test sample carried into the reaction region by said carrier gas;
a drift region through which said product ions travel in accordance with a charge and molecular size characteristic;
a shutter grid for selectively releasing said product ions from said reaction region into said drift cell drift region;
means for applying a drift gas stream of air to said to said drift region for carrying test sample having penetrated said membrane into said cell reaction region;
means for introducing sulfur dioxide dopant to said carrier gas stream of air and to said drift gas stream of air;
an ion current detector for detecting product ions transiting said cell drift region; and
means for measuring the transit times through said cell drift region of product ions generated in said cell reaction region and released into said cell drift region through said shutter grid;
means for measuring an ion current detected by said cell ion current detector at a time corresponding to the drift time of ions generated from said analyte gas in said cell reaction region to provide an ion current value;
whereby said sulfur dioxide dopant causes ions generated by said carrier gas stream and drift gas stream in said cell reaction region to have transit times through said cell drift region which are different from the transit times through said cell drift region of ions generated by the test sample.

28. The ion mobility spectrometer according to claim 27, whereby said sulfur dioxide dopant suppresses a componant of said measured ion current attributable to ions generated by test sample acid gasses with low charge affinities, said measured ion current being attributable mainly to ions generated by test sample acid gasses with high charge affinities.

29. The ion mobility spectrometer according to claim 27, whereby said means for allowing a limited amount of said test sample to penetrate said inlet region further comprises a gas permeable membrane.

30. The apparatus according to claim 27, wherein said sulfur dioxide doping means comprises a gas permeable tube immersed in said drift gas stream, and a gas permeable tube immersed in said carrier gas stream, whereby dopant in said tube permeates therethrough into said drift and carrier gas streams.

31. The apparatus according to claim 30, wherein said gas permeable tube introduces said dopant to each of said drift and carrier gas streams at a rate of about 365 nanograms per minute.

32. The apparatus according to claim 27, further comprising processing means for computing a quantity of an acid gas constituent in said test sample based on said ion current measured by said ion current measurement means.

33. The apparatus according to claim 32, wherein said processing means further comprises a memory for storing expected peak ion current data characteristic of said constituent acid gas in said test sample, said processing means comparing actual measured ion currents detected by said cell ion current detector to said expected peak ion current data and quantifying said constituent based on said comparison.

34. The apparatus according to claim 33, wherein said expected peak ion current data comprises a calibration curve relating said actual measured ion currents to said constituent concentration.

* * * * *